(12) United States Patent
Banes et al.

(10) Patent No.: US 6,721,667 B2
(45) Date of Patent: Apr. 13, 2004

(54) METHOD AND SYSTEM FOR MEASURING PROPERTIES OF DEFORMABLE MATERIAL SPECIMENS

(75) Inventors: Albert J. Banes, Hillsborough, NC (US); Melissa Marie Maloney, Carrboro, NC (US)

(73) Assignee: Flexcell International Corporation, McKeesport, PA (US)

( * ) Notice: Subject to any disclaimer, the term of this patent is extended or adjusted under 35 U.S.C. 154(b) by 0 days.

(21) Appl. No.: 10/361,810

(22) Filed: Feb. 10, 2003

(65) Prior Publication Data

US 2003/0182069 A1 Sep. 25, 2003

Related U.S. Application Data

(60) Provisional application No. 60/355,292, filed on Feb. 8, 2002.

(51) Int. Cl.$^7$ .............................. G01B 3/00; G01B 5/00; G01L 1/00
(52) U.S. Cl. ................................. 702/41; 702/33; 73/81
(58) Field of Search .............................. 702/33, 41, 42, 702/81, 117, 155, 156, 167, 170; 73/81, 108, 760, 788

(56) References Cited

U.S. PATENT DOCUMENTS 5,999,887 A * 12/1999 Giannakopoulos et al. ... 702/33

OTHER PUBLICATIONS

Lee TQ, Woo S L–Y, *A New Method for Determining Cross–sectional Shape and Area of Soft Tissues*, Journal of Biomechanical Engineering. vol. 110; pp. 110–114, 1988.

Peterson, R.H., Woo S L–Y, *A New Methodology to Determine the Mechanical Properties of Ligaments at High Strain Rates*; Journal of Biomechanical Engineering; vol. 108; pp. 365–367.

Woo S L–Y, Danto ID; Ohland KJ, Lee TQ, Newton PO, *The Use of a Laser Micrometer System to Determine the Cross–Sectional Shape and Area of Ligaments: A Comparative Study with two Existing Methods*; Transactions of the ASME; vol. 112, Nov. 1990; pp. 426–431.

Shrive NG, Lam TC, Damson E, Frank CB, *A New Method of Measuring the Cross–Sectional Area of Connective Tissue Structures*; Transactions of the ASME; vol. 110, May 1988; pp. 104–109.

Masahiko Noguchi, Toshiya Kitaura, Kazuya Ikoma, Yoshiaki Kusaka, *A method of in–vitro measurement of the cross–sectional area of soft tissues, using ultrasonography*, Journal of Orthopaedic Science (2002) vol. 7; pp. 247–251.

Nak Hyun Kim, Annette B Wysocki, Alan C Bovik, Kenneth R Diller, *A Microcomputer–Based Vision System for Area Measurement*; Comput. Biol. Med.; vol. 17; No. 3; pp. 173–183; 1987.

(List continued on next page.)

Primary Examiner—John Barlow
Assistant Examiner—John Le
(74) Attorney, Agent, or Firm—Webb Ziesenheim Logsdon Orkin & Hanson, P.C.

(57) ABSTRACT

Disclosed is a system for measuring mechanical properties of a deformable material specimen. The system includes a first gripping device for removably securing a first end of the specimen, a second gripping device for removably securing a second end of the specimen and an image acquisition device for producing image data reflective of a specified area of the specimen. Either the first gripping device or the second gripping device is movable in a first direction and in communication with the displacement measurement mechanism, which produces displacement data. The first gripping device or the second gripping device is also in communication with the load measurement mechanism for producing load data. Also disclosed is a method for measuring the mechanical properties of a deformable material specimen.

102 Claims, 2 Drawing Sheets

OTHER PUBLICATIONS

Ray Vanderby, Jr, Gene P Masters, James R Bowers, Ben K Graf, *A Device to Measure the Cross–Sectional Area of Soft Connective Tissues*, IEEE Transactions on Biomedical Engineering; vol. 18, No. 9, Oct. 1991; pp. 1040–1042.

F Iaconis, R Steindler, G Marinozzi, *Measurements of Cross–Sectional Area of Collagen Structures (Knee Ligaments) by Means of an Optical Method*, Journal of Biomechanics; vol. 20, No. 10, pp. 1003–1010; 1987.

* cited by examiner

METHOD AND SYSTEM FOR MEASURING PROPERTIES OF DEFORMABLE MATERIAL SPECIMENS

CROSS REFERENCE TO RELATED APPLICATIONS

This application claims the benefit of U.S. Provisional Patent Application Ser. No. 60/355,292, filed Feb. 8, 2002.

BACKGROUND OF THE INVENTION

1. Field of the Invention

The present invention relates generally to computer-implemented methods and automated systems for visually collecting geometrical, analytical measurements from deformable material specimens and determining mechanical properties and, in particular, to methods and systems for determining mechanical properties of tissue samples and other biomaterial.

2. Description of Related Art

Mechanical test machines are used routinely in engineering applications to determine material properties. These machines typically provide displacement data by using a linear variable differential transformer (LVDT) and force data or load data by means of a load cell. In order to convert the data generated or output by a load cell and linear variable differential transducer (LVDT) into values that describe the mechanical properties of the specimen or material being tested, the geometry of physical dimensions of the specimen must be determined. However, soft tissue samples are easily deformable and pose a particular challenge in geometrical or physical measurement.

Many prior art measurement processes rely on "contact methods" in which the process itself can affect the specimen dimensions. A non-contact method is needed for accurate measurement of this type of specimen. Further, soft tissues are highly extensible and viscoelastic. In order to track their significant dimensional changes in response to external loading forces, a real-time measurement method is required. Also, unlike harder, tougher biological specimens such as bone, cartilege, or inorganic samples such as glasses, plastics or metals that can be consistently machined to specific dimensions, soft tissue specimens and other biomaterial tend to contain inherent non-uniformities and are difficult to machine. The ability to concurrently collect dimensional measurements at multiple points on the specimen without influencing the dimensions being measured provides a real benefit in these and other applications of this nature.

In the article entitled "A New Method for Determining Cross-Sectional Shape and Area of Soft Tissues," by Lee, T. Q. and Woo, S. L-Y., published in the Journal of Biomechanical Engineering at 110:110–114 (1988), an assessment of the cross-sectional area of soft tissues using an image reconstruction technique is disclosed. This image reconstruction technique is based on measurements from collimated laser beams, and using this procedure, the actual shape of the specimen cross-section can be determined. However, this method does not provide the ability to measure cross-sectional area at multiple points along the length of the specimen simultaneously. In addition, this method does not allow for real-time measurements while the specimen is installed or loaded in a mechanical test machine. Further, this method does not include any instruction on how to perform property calculations or create specified reports or graphical displays of these properties. Still further, this method does not create a video record of the mechanical test or allow correlation of the data to this video.

Another method is disclosed in "A New Methodology to Determine the Mechanical Properties of Ligaments at High Strain Rates," by Peterson, R. H. and Woo, S. L-Y., published in the Journal of Biomechanical Engineering at 108:365–367 (1986). This method uses a video camera as a non-contact means for gathering straining measurements of soft tissues. In addition, this method discusses studying the strains at any specific area along the ligament substance to detect the variation of strains along the length of the tissue. However, this method does not calculate cross-sectional area and, therefore, cannot produce accurate results for certain mechanical property calculations that require this information. Also, this method does not include any methods or the ability to perform property calculations to create graphical reports and displays of the same. In addition, the data, such as the image data from the video record, is not correlated with the calculated mechanical property data.

"The use of a laser micrometer system to determine the cross-sectional shape and area of ligaments: a comparative study with two existing methods," by Woo, S. L., Danto, M. I., Ohland, K. J., Lee, T. Q. and Newton P. O., published in the Journal of Biomechanical Engineering at 112(4):426–31 (Nov. 1990) discloses a method of determining cross-sectional shape and area of soft tissues. The system disclosed in this article describes the use of a laser micrometer system to determine the cross-sectional area of ligaments. This system does not use a camera or any image data, instead using a static laser measurement system. While the system does allow for non-contact cross-sectional area measurements, it does not allow for measuring cross-sectional area at multiple points along the length of the specimen simultaneously. In addition, it does not provide real-time measurements while the specimen is installed or loaded in a mechanical test machine. In addition, the system does not include any software or methodology to perform property calculations or create graphical reports or display information. Still further, this system does not create any video record of the mechanical test or allow correlation of data to the video record.

Another method is disclosed in "A new method for determining cross-sectional shape and area of soft tissue," by Lee, T. Q. and Woo, S. L., published in the Journal of Biomechanical Engineering at 110(2): 110–4 (May 1988). As discussed above, this method does allow for the determination of cross-sectional area of soft tissues. This system uses a laser and does not allow for measuring of cross-sectional area at multiple points along the length of the specimen simultaneously. Further, the methodology does not allow for real-time measurements while the specimen is installed or loaded in a mechanical test machine. Further, this method does not include any software or methodology to perform property calculations or create reports or graphical displays of these calculations and, therefore, does not correlate the data obtained from the mechanical test to any video record of the same.

A further method is disclosed in "A new method of measuring the cross-sectional area of connective tissue structures," by Shrive, N. G., Lam, T. C., Damson, E. and Frank, C. B., published in the Journal of Biomechanical Engineering at 110(2): 104–9 (May 1988). This method allows for the measurement of cross-sectional area of connective tissue structures. The method uses an instrument to measure the thickness of the tissue as a function of position along the width of the tissue. This method does not use a camera and does not allow for the measuring of cross-sectional area at multiple points along the length of the specimen simultaneously. The method does not disclose the use of real-time measurements conducted while the specimen is installed or loaded in a mechanical test machine. No methodology or software is disclosed that can perform the property calculations or create reports or graphical displays of these calculations. The method does not create a video record of the mechanical test or allow the correlation of the video to the calculated data. In addition, while this method does claim to be non-destructive, it does not claim to be a non-contact method.

"A method of in-vitro measurement of the cross-sectional area of soft tissues, using ultrasonography," by Noguchi, M., Kitaura T., Ikoma, K. and Kusaka Y., published in the Journal of Orthopedic Science at 7(2): 247–51 (2002) discloses yet another method that determines the cross-sectional area of soft tissues in a non-contact manner. The method uses ultrasonography, and not a camera, and further does not allow for the measurement of cross-sectional area at multiple points along the length of the specimen simultaneously. Further, the method does not allow for real-time measurements while the specimen is installed or loaded in a mechanical test machine. No software or methodology is disclosed to perform property calculations or create reports or graphical displays of these calculations, and no video record of the mechanical test or correlation of the data to this video is taught in this publication.

"A microcomputer-based vision system for area measurement," by Kim, N. H., Wysocki, A. B., Bovik, A. C. and Diller, K. R., published in Computers in Biology and Medicine at 17(3): 173–83 (1987) discloses a microcomputer-based vision system for area measurements. The algorithm disclosed allows the use of images in determining areas and cross-sections of cell and multicellular tissue. These measurements are gained in a non-contact manner and a camera is used. However, this system does not allow for real-time measurements while the specimen is installed or loaded in a mechanical test machine. Further, no software or methodology is described, which would perform property calculations and create reports or graphical displays of these calculations. This system is not designed for use in conjunction with mechanical tests, and therefore does not allow correlation of any data with video. It does not appear that this system can be used for measuring cross-sectional area at multiple points along the length of the specimen simultaneously.

"A device to measure the cross-sectional area of soft connective tissues," by Vanderby, R., Jr., Masters, G. P., Bowers, J. R. and Graf, B. K., published in IEEE Transactions on Biomedical Engineering at 38(10): 1040–2 (Oct. 1991) discloses a device to measure the cross-sectional area of soft connective tissues ex vivo. Displacement transducers are used to output information to a personal computer. This device does not use a camera, but uses displacement transducers and the device does not allow for the measurement of cross-sectional area at multiple points along the length of the specimen simultaneously. Further, the device does not provide real-time measurements while the specimen is installed or loaded in a mechanical test machine. This device does not include any software or methodology to perform property calculations and create reports and/or graphical displays of these calculations. Still further, the device does not create a video record of the mechanical tests or allow correlation of data to this video.

"Measurements of cross-sectional area of collagen structures (knee ligaments) by means of an optical method," by Iaconis, F., Steindler, R. and Marinozzi G., published in Journal of Biomechanical Engineering at 20(10):1003–10 (1987) discloses yet another methodology to measure cross-sectional area of collagen structures by using an optical system. This methodology does not allow for the measurement of cross-sectional area at multiple points along the length of the specimen simultaneously. In addition, the system does not permit real-time measurements while the specimen is installed or being loaded in a mechanical test machine and, further, does not include any software or method to perform property calculations or create reports or graphical displays of these calculations. Area calculations are not performed in the context of a mechanical test, and, therefore, no such video record can be correlated to the produced data. This system requires sectioning of the specimen and is therefore destructive and cannot be non-contact in nature.

SUMMARY OF THE INVENTION

It is, therefore, an object of the present invention to provide a method and system for measuring the mechanical properties of deformable materials, such as tissue and other such biomaterial. It is another object of the present invention to provide a method and system for measuring mechanical properties of deformable materials that uses an optical system, such as camera devices, and simultaneously measures the cross-sectional area of the specimen at multiple points along the length of the specimen. It is another object of the present invention to provide a method and system for measuring the mechanical properties of deformable materials that uses real-time measurements while the specimen is installed or being subjected to load in a mechanical test machine. It is a still further object of the present invention to provide a method and system for measuring mechanical properties of deformable materials that accurately performs property calculations and creates reports and graphical displays of these calculations to the user. It is yet another object of the present invention to provide a method and system for measuring mechanical properties of deformable materials that creates a video record of the mechanical test and allows the correlation of data and calculations to this video. It is a still further object of the present invention to provide a method and system for measuring mechanical properties of deformable materials that conducts cross-sectional area measurements in a non-contact manner.

Accordingly, we have invented a system for measuring mechanical properties of a deformable material specimen. The system includes a first gripping device for removably securing a first end of the specimen, and a second gripping device for removably securing a second end of the specimen. An image acquisition device is positioned with respect to the specimen and produces image data reflective of a specified area of the specimen. Either the first gripping device or the second gripping device is movable in a first direction and is in communication with the displacement measurement mechanism. This displacement measurement mechanism produces displacement data reflective of the position of the movable gripping device. The system also includes a load measurement mechanism in communication with either the first gripping device or the second gripping device. This load measurement mechanism produces load data reflective of the force experienced by the first gripping device or the second gripping device.

In another aspect of the present invention, a computer-implemented method is disclosed for determining mechanical properties of a deformable material specimen. This method includes the steps of: (a) removably securing a first end of the specimen in a first gripping device; (b) removably securing a second end of the specimen in a second gripping device; (c) obtaining image data reflective of at least one physical dimension of a portion of the specimen in an initial state; (d) applying a load to the specimen by moving either the first gripping device or the second gripping device; (e) measuring the displacement of the moved gripping device therefore producing displacement data; (f) measuring the load placed upon the specimen, thereby producing load data; and (g) calculating a specimen property based at least partially on the image data, the displacement data and the load data.

In a preferred embodiment of the present system, a control mechanism is included and is in communication with the image acquisition device, the displacement measurement mechanism and the load measurement mechanism. This control mechanism receives respective image data, displacement data and load data from the image acquisition device, the displacement measurement mechanism and the load measurement mechanism. The control mechanism is in communication with a visual display device which displays information and data direct to the image data, the displacement data, the load data or any data calculated by the control mechanism.

In another preferred embodiment, the displacement measurement mechanism is a linear variable differential transformer and the load measurement mechanism is a load cell. Further, the image acquisition device is preferably a first camera device and a second camera device, each having a field of vision. The first camera device and the second camera device are positioned at 90 degrees with respect to each other in order to collect specified area information of separate surfaces of the specimen. Further, the first camera device and the second camera device may be connected to an image acquisition control mechanism, which serves to receive, process and transmit information to the control mechanism.

The present invention, both as to its construction and its method of operation, together with the additional objects and advantages thereof, will best be understood from the following description of exemplary embodiments when read in connection with the accompanying drawings.

BRIEF DESCRIPTION OF THE DRAWINGS

FIG. 1 is a schematic view of a system for measuring mechanical properties of a deformable material specimen according to the present invention;

FIG. 2a is a front view of a calibration target used in the system of the present invention;

FIG. 2b is a side view of the calibration target of FIG. 2a; and

DESCRIPTION OF THE PREFERRED EMBODIMENTS

Figures 1, 2A, 2B:
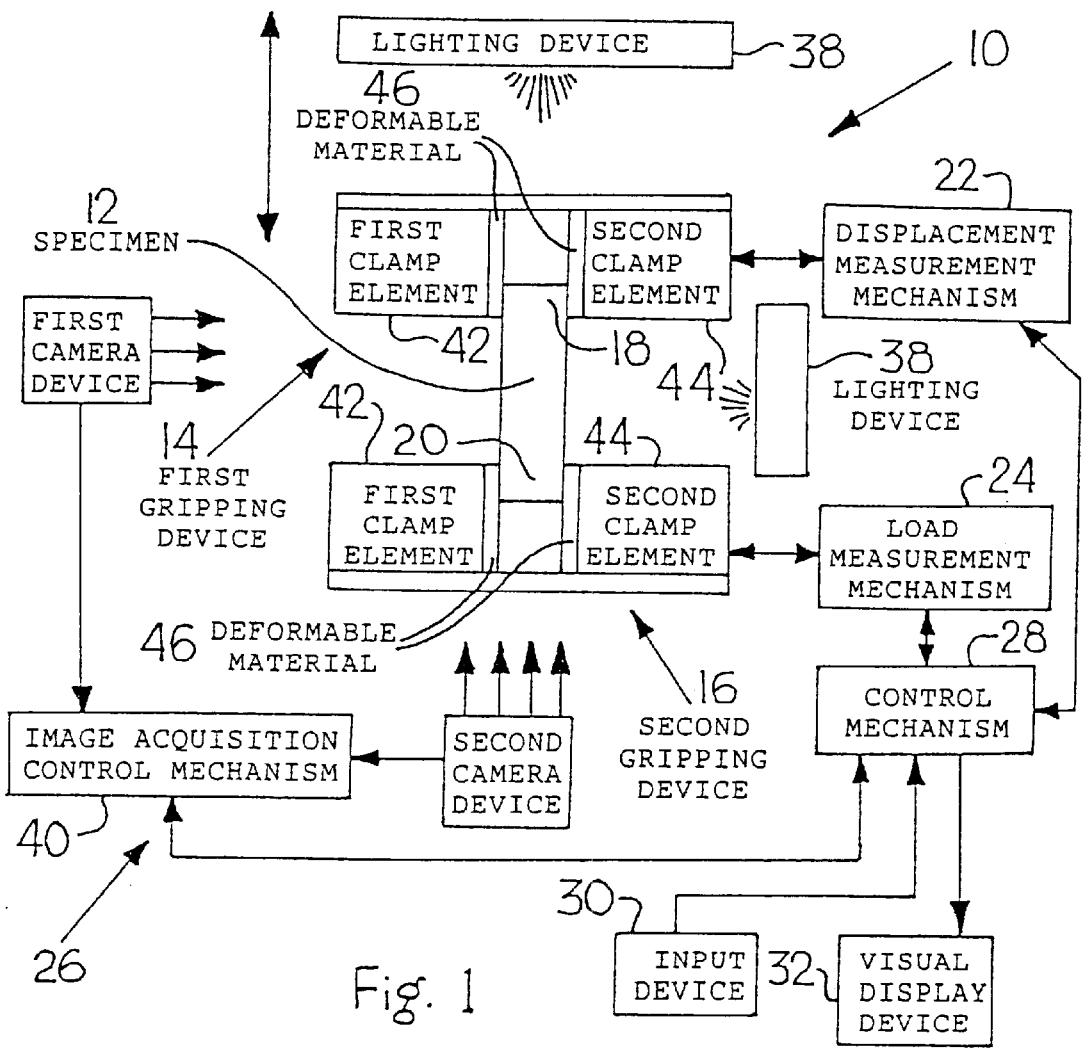

The present invention is a system 10 for measuring mechanical properties, such as material or structural properties, of a deformable material specimen 12, and is schematically illustrated in FIG. 1. The system 10 includes a first gripping device 14 and a second gripping device 6. The first gripping device 14 is capable of removably securing a specimen first end 18, and similarly, the second gripping device 16 is capable of removably securing a specimen second end 20.

The system 10 also includes at least one image acquisition device 26 for producing image data that is reflective of a specified area of the specimen 12. Either the first gripping device 14 or the second gripping device 16 is movable in a first direction, and in a preferred embodiment, this is an up-and-down or in a "z" direction. In a still further preferred and non-limiting embodiment, the first gripping device 14 is movable, while the second gripping device 16 is static. Therefore, the movable device or the first gripping device 14 is in communication with a displacement measurement mechanism 22. This displacement measurement mechanism 22 produces displacement data or positional data with respect to the z-axis that is reflective of a position of the first gripping device 14. This position, in turn, can be directly correlated to one or more specified positions or areas on the specimen 12.

Either the first gripping device 14 or the second gripping device 16 is in communication with a load measurement mechanism 24. In a preferred embodiment, the non-moving or second gripping device 16 is in communication with the load measurement mechanism 24, which produces load data that is reflective of the force experienced by the second gripping device 16. As with the displacement data, the load data measured by the load measurement mechanism 24 is directly reflective of and correlatable to the force experienced by the specimen 12 as it is being stressed or strained.

The system 10 also includes at least one image acquisition device 26 which gathers and produces image data reflective of a specified area of the specimen 12. All of the image acquisition device 26, the displacement measurement mechanism 22 and the load measurement mechanism 24 are in communication with a control mechanism 28. This control mechanism 28 receives and processes the image data from the image acquisition device 26, the load data from the load measurement mechanism 24 and the displacement data from the displacement measurement mechanism 22. In a preferred embodiment, the control mechanism 28 is in the form of a personal computing device, such as a personal computer, a laptop, or other similar system. In addition, the control mechanism 28 is able to receive various input data sources, including the above-discussed data, process this data, perform calculations and other similar operations and output the results in a visual format.

An input device 30 is included in order to allow the user to operate the control mechanism 28 and, further, operate one or more of the components and subcomponents of the system 10. Any typical input device 30 is envisioned, such as a keyboard, a lightpen, a mouse, etc. The control mechanism 28 is also in communication with a visual display device 32, which visually displays information and data directed to the image data, the displacement data, the load data, or other various inputs and outputs based upon data processed by the control mechanism 28.

In order to improve the quality and accuracy of the image data that is reflective of a specified area of the specimen 12, it is also envisioned that the image acquisition device 26 be movable with respect to the stationary specimen 12. In this manner, the image acquisition device 26 could be located in a position that gives the "best fit" for the specified area and/or the cross-sectional area of the specimen 12. This could be accomplished by removably attaching the image acquisition device 26 to a motorized unit or mount. Further, this motorized mount could be in communication with and controlled by the control mechanism 28. Such optimization is particularly desirable when working with non-uniformly shaped specimens 12, as is typically the case with biomaterial. For example, optimization is required when working with an elliptical-shaped specimen 12 in order to obtain the correct diameter and cross-sectional area at a specified portion of the specimen 12. Therefore, the ability to take a 360 degree view around the specimen 12 and/or automatically take the gage length at a specific portion of the specimen 12 can be achieved through the above-described optimization functionality.

As part of its ability to process data, the control mechanism 28 can calculate one or more properties of the specimen 12 based at least partially upon the image data, the displacement data and the load data. Once the calculation has been performed, the control mechanism 28 communicates the results to the visual display device 32, which displays to a user the information and data regarding the properties of the specimen 12.

Typically, the system 10 is placed upon a flat work surface which is isolated from vibration. In a preferred embodiment, the displacement measurement mechanism 22 is a linear variable differential transformer that allows for precise, position and displacement data measurement. In addition, the load measurement mechanism 24 may be a load cell.

In order to gather proper image data, in a preferred embodiment, the image acquisition device is a first camera device 34 and a second camera device 36. However, a single image acquisition device 26 can be used in conjunction with a directional or positionable optical system. For example, appropriately positioned mirrors may be used. In the present embodiment, both the first camera device 34 and the second camera device 36 have a respective field of vision. In order to maximize and correlate the image data, the first camera device 34 field of vision is positioned at 90 degrees with respect to the second camera device 36 field of vision. The first camera device 34 field of vision may be directed towards a first surface of the specimen 12, for example, the front surface, while the second camera device 36 field of vision is directed towards a second surface of the specimen 12, for example a side surface. The system 10 may also include a lighting device 38 positioned on a side surface of the specimen 12 immediately opposite the side surface of the specimen 12 upon which the field of vision of either the first camera device 34 or the second camera device 36 is focused. In a preferred embodiment, two lighting devices 38 are used, one opposite each of the first camera device 34 and the second camera device 36. The lighting device 38 creates silhouettes of the specimen 12, improves contrast and allows for better image data collection.

As discussed above, it is envisioned that both the first camera device 34 and the second camera device 36 be movable and/or located on a motorized or movable mount or platform. In addition, in order to maintain the proper alignment between the first camera device 34 and the second camera device 36, their movement can be in a controlled and static relationship with respect to each other. When using the lighting devices 38, these lighting devices 38 could also be on a motorized unit or movable mount, and, again, the movement of the lighting devices 38 could be aligned with and static with respect to the movement of a respective first camera device 34 and a second camera device 36. All of these movable mounts may be in communication with and operable by the control mechanism 28. Again, the movement of the first camera device 34, the second camera device 36 and their respective lighting devices 38 allow the user to optimize the geometry and, therefore, the accuracy of the image data collected by the first camera device 34 and second camera device 36.

It may also be preferable, when using the first camera device 34 and the second camera device 36, to use an image acquisition control mechanism 40 for receiving data from the first camera device 34 and the second camera device 36. The image acquisition control mechanism 40 is further capable of collecting, processing and transmitting the image data to the control mechanism 28. The image acquisition control method 40 may be in the form of a printed circuit board that is in communication with or integrated with the control mechanism 28 or personal computer.

The specimen 12 can be any number of deformable materials. For example, the specimen 12 can be a soft or hard tissue, a biomaterial, a deformable material, bio-artificial material or viscoelastic material. For example, the specimen 12 can include bio-artificial tendon (BAT) constructs fabricated using various culturing systems or other tissue engineered material.

A user is permitted to specify a portion of the specimen 12, and the portion of the specimen 12 can include one or more regions of interest located within the field of vision of the image acquisition device 26. In the preferred embodiment, using the first camera device 34 and the second camera device 36, the user specifies a portion of the specimen 12 having multiple regions of interest in both the first camera device 34 field of vision and the second camera device 36 field of vision. This allows the user to isolate a specific region of interest in one camera view and the system 10 will allow the specified region of interest to be communicated between and duplicated on the other camera device. This functionality allows for measuring the cross-sectional area of the specimen at multiple points along the specimen 12 simultaneously. It is also envisioned that the image acquisition device 26 may be used to calculate strain and stress between gage marks or set points on the surface of the specimen 12.

The image data collected from the image acquisition device 26 may be used to calculate one or more cross-sectional areas of the specimen 12 in the region of interest individually or simultaneously. The cross-sectional area of the specimen 12 may be calculated by summing pixels across the specimen 12 in the first camera device 34 field of vision and/or the second camera device 36 field of vision. The summed pixels are then converted to a specified unit of measurement, for example millimeters. As discussed hereinafter, the image acquisition device 26 may first be calibrated and a conversion factor calculated using images and image data from the first camera device 34 and the second camera device 36. The conversion factor and results are checked against each other to ensure accuracy and the pixel-to-millimeter conversion factor is used by the control mechanism 28 for subsequent testing. In addition, the conversion factor is only valid as long as the configuration and positioning of the components and the subcomponents of the system 10 remain the same. If any adjustments are made, the calibration process should be repeated. Using this conversion, the control mechanism 28 can directly calculate the cross-sectional area of the specimen 12 in millimeters or other unit of measurement.

As is known in the art, in order to determine cross-sectional area of the specimen 12, the basic geometry of the specimen 12 should be determined. For example, a substantially flat specimen would require width and depth to determine cross-sectional area, while an oval or elliptical specimen 12 would require diameter. Therefore, the control mechanism 28, using the image acquisition device 26, is capable of determining how the cross-sectional area of the specimen 12 should be calculated. Further, the conversion factor typically gives a dimension, such as diameter, in millimeters. The control mechanism 28 can then calculate the area based on these diameters.

In a preferred embodiment, the first gripping device 14 and the second gripping device 16 both include a first clamp element 42 and a second clamp element 44. The first clamp element 42 and the second clamp element 44 are actuateable towards and away from each other. When the first clamp element 42 and the second clamp element 44 are moved towards each other, this movement results in a gripping or clamping function. Accordingly, when the first clamp element 42 and the second clamp element 44 are moved away from each other, this movement results in a release function. The gripping function and release function may be driven by any contemplated force, such as by hand, knobs or other similar device driven by human force. It is also envisioned that the control mechanism 28 be in communication with the first gripping device 14 and the second gripping device 16 and the movement of the first clamp elements 42 and the second clamp elements 44 are accomplished through commands and data gathered, processed and transmitted by the control mechanism 28. The first gripping device 14 and the second gripping device 16 can be freezing grips, drum grips, custom grips, hydraulic controllable grips, etc.

One or both of the first clamp element 42 and the second clamp element 44 include an interface surface for contacting the specimen 12. This interface surface may be removable and is used to hold the specimen 12 in place during testing. Further, the interface surface may be manufactured from or coated with a deformable layer of material 46. This deformable layer of material 46 may be rubber, a synthetic material, a polymer, etc. In a preferred embodiment, the deformable layer of material 46 is rubber, which is soft enough to deform around the specimen 12, rather than pinching it and creating a large stress concentration at the edge of the first gripping device 14 and the second gripping device 16. Still further, the deformable layer of material 46 may include a textured surface, which increases the contact area and helps to prevent the specimen 12 from slipping in the first gripping device 14 and the second gripping device 16. It is also envisioned that the first gripping device 14 and the second gripping device 16 can be freezing grips, drum grips or custom grips capable of removably securing at least a portion of the specimen 12 for testing.

After the specimen 12 is secured between the first gripping device 14 and the second gripping device 16, the movable gripping device (14, 16), in this embodiment the first gripping device 14, is actuated. This actuation exerts a load on the specimen 12. In addition, it is also envisioned that this actuation is controlled by the control mechanism 28. It is important that the displacement of the first gripping device 14 provide for highly-controlled adjustment of the position.

The exerted load may be in any number of profiles. For example, the specimen 12 may be loaded in a ramp profile, a step profile, a cyclic profile, a patterned profile, a predetermined profile, a user-specified load and a static load. When the specimen 12 is loaded in a ramp profile, the first gripping device 14 is displaced at a constant rate with respect to a preset target position. However, the specimen 12 may also be loaded in a cyclic pattern over an extended period, and the specimen 12 may be protected in a nutritive bioreactor. This will allow for the measurement of fatigue strength. Also, applying a static load to the specimen 12 over an extended period, again, with the specimen 12 protected from dehydration, would allow for the determination of the creep characteristics of the specimen 12. If the load measurement mechanism 24 includes the appropriate sensitivity characteristics, the system 10 could also be used to measure the contractile force of the specimen 12. Therefore, stimulating the construct or specimen 12 to contract via a ligand or an electric pulse, the resulting force could be measured by the load measurement mechanism 24 or load cell.

The load data generated by the load exerted on the specimen 12, as measured through the second gripping device 16, is used to calculate one or more specimen 12 mechanical (material, structural) properties. For example, the specimen 12 property can be engineering stress, true stress, engineering strain, true strain, fatigue strength, creep characteristics, ultimate tensile strength, elastic modulus, contractile force, stiffness, toughness, ultimate stress, strain at ultimate stress, strain energy density, ultimate load, etc. The control mechanism 28 includes the appropriate data and algorithms for calculating any one or more of the above-listed mechanical properties of the specimen 12.

The present invention is also directed to a computer-implemented method of determining the mechanical properties of a deformable material specimen 12. This method includes the steps of: (a) removably securing the specimen first end 18 in the first gripping device 14; (b) removably securing the specimen second end 20 in a second gripping device 16; (c) obtaining image data reflective of at least one physical dimension of a portion of the specimen 12 at an initial state; (d) applying a load to the specimen 12 by moving either the first gripping device 14 or the second gripping device 16; (e) measuring the displacement of the moved gripping device (14, 16), thereby producing displacement data; (f) measuring a load placed upon the specimen 12, thereby producing load data; and (g) calculating one or more properties of the specimen 12 based at least partially upon the image data, the displacement data and the load data. As discussed above, after the specimen 12 has been loaded, the image data, again reflective of a physical dimension of a portion of the specimen 12, is obtained at the loaded state of the specimen 12.

As the image data is received from the image acquisition device 26, this data can be immediately stored by the control mechanism 28 and/or immediately displayed to the user in a real-time format. For example, the visual information and data can be in a graphical format, a video format, an audio-visual format and a textual format. This allows the user to view a streaming video of the experiment while it is being conducted, together with graphic or numeric mechanical property data simultaneously or immediately thereafter, in the form of a property of the specimen 12. Therefore, this permits the user to immediately see the calculation or results produced by the control mechanism 28 together with the video image in a simultaneous and real-time format. In addition, since the control mechanism 28 is collecting and storing the data, the user can then, after the experiment is complete, review the image data and calculation and results at any one or more points in time during the entire testing process. Still images can be taken from the video data in order to examine specific and discrete time points and their associated specimen 12 property results during a loaded state.

As discussed above, it is preferable to properly calibrate the image acquisition device 26 by calibrating the field of vision prior to collecting image data relative of the specimen 12. In order to perform the calibration process, the user should obtain image data that is reflective of at least one physical dimension of a portion of a calibration target 48. As seen in FIGS. 2a and 2b, the calibration target 48 may be substantially similar in size and shape to a portion of specimen 12.

The field of vision of the image acquisition device 26, which, in a preferred embodiment, is a first camera device 34 and a second camera device 36, is adjusted by adjusting the position of the camera devices (34, 36). The camera device (34, 36) positions are adjusted in the x-direction, the y-direction, the z-direction, for pitch, for roll and for yaw. The first camera device 34 field of vision and the second camera device 36 field of vision should be oriented such that both fields of vision are directed to a similar area on the calibration target 48. Both cameras should be adjusted until they are oriented in a position that is directly in-line with the target, substantially perpendicular to the field of vision of the other camera device (34, 36) and the field of vision of one camera device (34, 36) captures a view of the same area on the calibration target 48 as the other camera device (34, 36).

After camera device (34, 36) adjustment, the lighting devices 38 are adjusted to provide clear image data with good contrast. In order to assist in these adjustments, the control mechanism 28 also allows the user to see a video stream from each of the camera devices (34, 36) without actually collecting any data. During the calibration process, opposite edge locations on the calibration target 48 are detected and the pixels between the opposite edge locations in the field of vision are summed. As discussed above, it is also possible to allow the user to isolate a specific region of interest in one camera device (34, 36) view and duplicate a similar region of interest shape and position in the other camera device (34, 36) view. This allows the views to match size and vertical position as seen by each respective camera device (34, 36).

This process is repeated for multiple opposite edge locations on the calibration target 48. An average summation for these multiple opposite edge locations is calculated. Together with the known dimensions of the calibration target 48, the control mechanism 28 calculates a pixel-to-millimeter conversion factor, and this conversion factor is calculated using images from the first camera device 34 and the second camera device 36. The results are checked against each other to ensure accuracy, and the conversion factor is used by the control mechanism 28 to calculate millimeter measurements of a specimen 12. Again, if any of the system 10 components are moved, the calibration process should be repeated.

The use of the image acquisition device 26, or in a preferred embodiment the first camera device 34 and the second camera device 36, allows for the collection of information and data simultaneously over a region, rather than at a single point. Using the multiple region of interest lines, spread evenly over a user-defined portion of the specimen 12, helps to ensure that the area with the smallest diameter is identified. With each region of interest line in each of the first camera device 34 field of vision and the second camera device 36 field of vision, the control mechanism 28 identifies the first and last edges of the specimen 12 and measures the distance, in pixels, between the two identified edges. The cross-sectional geometry of the specimen 12 may be oval, and thus, the measured distances are representative of diameters. However, the present method works with any size and shape of specimen 12. The pixel-spaced diameter measurements are then converted to millimeters using the conversion factor determined during calibration. This conversion may also be completed dynamically using the image data.

In order to integrate the outputs from the first camera device 34 and the second camera device 36, the data should first be synchronized. The control mechanism 28 uses time stamps for the different output files to accomplish this task. First, the control mechanism 28 calculates when each image was collected and it interpolates between these points to find the force and displacement values at the corresponding times. The user may specify one or more material properties to be measured and/or calculated. For the calculation of engineering stress, the specimen 12 initial cross-sectional area ($A_0$) is required. The control mechanism 28 determines this value by finding the minimum cross-sectional area detected in the first frame of video data (time=0) and assigning this as $A_0$. For biological samples, there may be notable differences in the cross-sectional area along the length of the specimen 12, and if this is the case, the specimen 12 is most likely to break at the point of the smallest area.

In order to determine the initial cross-sectional area ($A_0$) for the entire specimen 12, and assuming a substantially oval cross-sectional geometry for the specimen 12, the following formula may be used:

$$A_0 = \left[\frac{\pi}{4}(D_{camera1} * D_{camera2})\right]_{0,\,min}$$

where D=diameter
The initial cross-sectional area ($A_0$) is then combined with the load measurement mechanism 24 load data at the same point in time in order to calculate the stress as follows:

$$\sigma_e = \frac{F_t}{A_0}$$

Engineering Stress ($\sigma_e$)
where
  $F_t$=Force at time, t
  $A_0$=initial cross-sectional areas
The displacement at the same point in time is combined with the initial gage length of the specimen 12 in order to calculate strain as follows:

$$\varepsilon_e = \frac{(y_{displacement})}{L_0}$$

Engineering Strain ($\epsilon_e$)
where
  $y_{displacement}$=the change in length of the specimen at time, t
  $L_0$=the original length of the specimen
The slope of the engineering stress-strain curve in the linear region gives the elastic modulus (E) of the specimen 12. The highest engineering stress value measured for a particular test is the ultimate tensile strength (UTS) of the specimen 12.

The control mechanism 28 and method is not limited to the measurements of only engineering stress and strain. As discussed above, other mechanical properties can be calculated by adding the appropriate measures and equations to the control mechanism 28. For example, true stress could be calculated by using the real-time cross-sectional area ($A_c$) rather than the initial cross-sectional area ($A_0$). The region of interest lines used to calculate $A_c$ must move at a rate proportional to the specimen 12 stretch, so that they are "locked-on" to fixed positions on the specimen 12. The method and system 10 also provides for the user to define this stretch rate.

Figure 3:
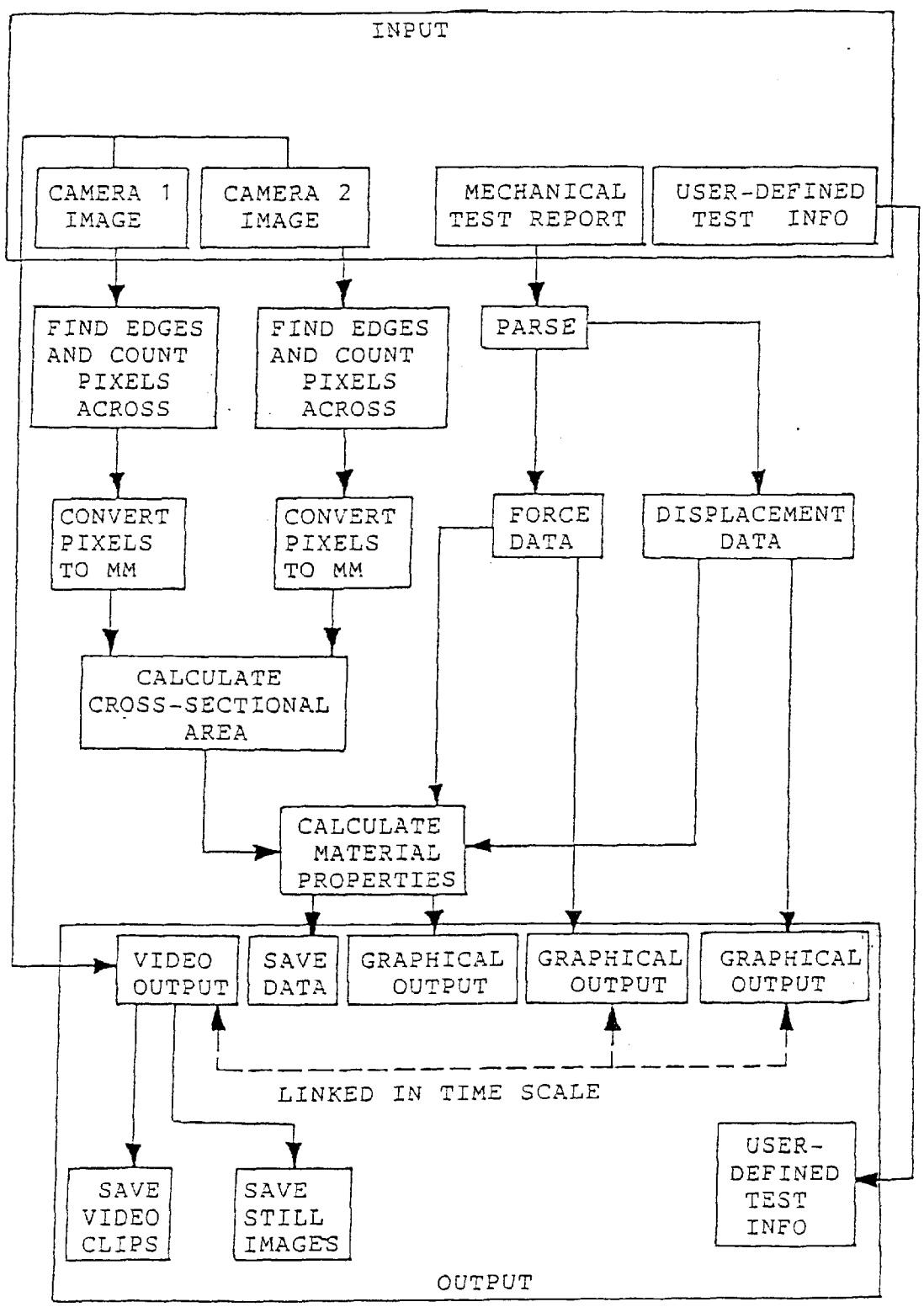
FIG. 3 is a flow diagram of a method for measuring the mechanical properties of a deformable material specimen according to the present invention.

A preferred embodiment of the method is illustrated in schematic form in FIG. 3. In a preferred application of the system 10 and method, the process is as follows. The specimen 12 is installed, the crosshead is moved to a starting position and the load measurement mechanism 24 is tared. The method and control mechanism 28 provides a video data streaming mode in order to view the specimen 12 position via the first camera device 34 and the second camera device 36 as it is being loaded. Carefully handling the specimen 12 with tweezers or forceps, the surface tension of the wet specimen 12 can be used to "adhere" it in place on the clamp elements (42, 44). In order to ensure the correct focus, the specimen 12 position should be adjusted as necessary until it is centered at the midpoint of the first gripping device 14 and the second gripping device 16. Further, the specimen 12 should be taut and vertically aligned in both directions. Once the positioning is complete, the data collection parameters for both the system 10, including the image acquisition device 26, are input into the control mechanism 28 via the input device 30. Data collection is then started. A large combined-view from the first camera device 34 and the second camera device 36 is shown on the visual display device 32 during the test.

Prior to starting any data acquisition, the user inputs test details on the control mechanism 28 via the input device 30. For example, such inputs can include the test stretch rate (rate at which the regions of interest lines will move along the specimen during the test), the data collection rate in frames per second (maximum rate limited by the hardware configuration, e.g., camera, RAM, processor or speed and by the complexity of the calculation specified in the software), and test information (optional reference text, such as specimen 12 description). This information and data are saved along with the data files for future reference.

While the test is being run, video image data from the first camera device 34 and the second camera device 36 is collected and stored in a temporary file, and further, the data from the displacement measurement mechanism 22 and the load measurement mechanism 24 is written to a text file that is exported to a user-specified file path. At the completion of the test, the method integrates these two data files to provide the user with a graphical display from the visual display device 32. This display can be used for viewing test results immediately following data acquisition or for reviewing results of earlier tests.

It is also envisioned that the computer-implemented method may include the following features: display of the video data in a "player" format (e.g., play, stop, rewind, fast-forward); display of the displacement data and load data plotted versus time; moving cursor on the force (load) and displacement graph that moves at the same rate that the video and image data progresses (allowing the user to relate events in the video to features of the graph); automatic calculation of the elastic modulus based on user-specified position of drag-and-drop cursors demarking the start and end points of the linear region of a stress-strain curve; editing of the video image data into shorter video clips or still frames; exporting of the calculated material specimen 12 property data into a text file; and review of the test information input by the user at the start of the test. Overall, the method may be in the form of a software program run by the control mechanism 28 and capable of controlling the process, performing the calculations, communicating information to or from the input device 30 and the visual display device 32, controlling the various components and subcomponents of the system 10, and performing all other related control features of the system 10.

In this manner, the present invention provides a system 10 and method for measuring mechanical properties of a deformable material specimen 12. This is a non-contact method and does not affect the specimen 12 while it is being subjected to load. Further, the method and system 10 allow for real-time measurements while the specimen 12 is installed or being subjected to load in a mechanical testing application, as opposed to a separate off-line procedure. The method on the control mechanism 28 includes the appropriate methodology to perform property calculations and create reports and graphical displays of these calculations. In addition, the method and system 10 create an image data and video record of the mechanical test and allow the correlation of this data to one or more points of the video.

This invention has been described with reference to the preferred embodiments. Obvious modifications and alterations will occur to others upon reading and understanding the preceding detailed description. It is intended that the invention be construed as including all such modifications and alterations.

What is claimed is:

1. A system for measuring mechanical properties of a deformable material specimen, comprising:
   a first gripping device configured to removably secure a first end of the specimen;
   a second gripping device configured to removably secure a second end of the specimen; and
   at least one image acquisition device configured to produce image data reflective of a specified area of the specimen;
   wherein at least one of the first gripping device and the second gripping device is movable in a first direction and in communication with a displacement measurement mechanism configured to produce displacement data reflective of a position of the at least one of the first gripping device and the second gripping device;
   wherein at least one of the first gripping device and the second gripping device is in communication with a load measurement mechanism configured to produce load data reflective of the force experienced by the at least one of the first gripping device and the second gripping device.

2. The system of claim 1, further comprising a control mechanism in communication with at least one of the image acquisition device, the displacement measurement mechanism and the load measurement mechanism and configured to receive at least one of respective image data, displacement data and load data therefrom.

3. The system of claim 2, further comprising a visual display device in communication with the control mechanism and configured to visually display information and data directed to at least one of the image data, the displacement data and the load data to a user.

4. The system of claim 2, wherein the control mechanism is further configured to calculate at least one specimen property based at least partially upon at least one of the image data, the displacement data and the load data.

5. The system of claim 4, further comprising a visual display device in communication with the control mechanism and configured to visually display information and data directed to at least one of the image data, the displacement data, the load data and the calculated specimen property to a user.

6. The system of claim 1, wherein the displacement measurement mechanism is a linear variable differential transformer.

7. The system of claim 1, wherein the load measurement mechanism is a load cell.

8. The system of claim 1, wherein the image acquisition device comprises a first camera device with a first camera device field of vision and a second camera device with a second camera device field of vision.

9. The system of claim 8, wherein the first camera device field of vision is positioned at 90 degrees with respect to the second camera device field of vision.

10. The system of claim 8, wherein a user is permitted to specify a portion of the specimen having at least one region of interest in at least one of the first camera device field of vision and the second camera device field of vision.

11. The system of claim 10, wherein the at least one region of interest can be communicated between and duplicated on the first camera device and the second camera device.

12. The system of claim 10, wherein the image data is used to calculate at least one cross-sectional area of the specimen in the region of interest.

13. The system of claim 12, wherein the cross-sectional area is calculated by summing pixels across the specimen in the at least one of the first camera device field of vision and the second camera device field of vision.

14. The system of claim 13, wherein the summed pixels are converted to a specified unit of measurement.

15. The system of claim 8, wherein the first camera device is positioned such that the first camera device field of vision is directed at a front surface of the specimen and the second camera device is positioned such that the second camera field of vision is directed at a side surface of the specimen.

16. The system of claim 1, wherein the image acquisition device includes at least one field of vision directed to a side surface of the specimen.

17. The system of claim 16, further comprising a lighting device positioned on a side surface of the specimen immediately opposite the side surface of the specimen upon which the field of vision is directed.

18. The system of claim 17, wherein the lighting device is in operable communication with a positioning device configured to move the lighting device between desired positions with respect to the specimen.

19. The system of claim 18, wherein the positioning device is in operable communication with the image acquisition device and configured to move the image acquisition device between desired positions with respect to the specimen in a substantially fixed position with respect to the lighting device.

20. The system of claim 19, wherein the positioning device is motorized and controlled by a control mechanism.

21. The system of claim 1, wherein the image acquisition device is in operable communication with a positioning device configured to move the image acquisition device between desired positions with respect to the specimen.

22. The system of claim 21, wherein the positioning device is motorized and controlled by a control mechanism.

23. The system of claim 1, further comprising an input device in communication with a control mechanism and configured to transmit data to the control mechanism, the control mechanism in communication with at least one of the image acquisition device, the displacement measurement mechanism and the load measurement mechanism and configured to receive at least one of respective image data, displacement data and load data therefrom.

24. The system of claim 1, wherein the image acquisition device is in communication with an image acquisition control mechanism configured to collect, process and transmit the image data.

25. The system of claim 1, further comprising a visual display device configured to visually display the image data to a user.

26. The system of claim 1, wherein the specimen is one of soft tissue, biomaterial, deformable material, hard tissue, bioartificial material and viscoelastic material.

27. The system of claim 1, wherein at least one of the first gripping device and the second gripping device comprise a first clamp element and a second clamp element configured to be moved towards each other in a gripping function and away from each other in a release function.

28. The system of claim 27, wherein the first clamp element and the second clamp element have an interface surface configured to contact the specimen.

29. The system of claim 28, wherein the interface surface is coated with a substantially deformable layer of material.

30. The system of claim 29, wherein the deformable layer of material is one of rubber, a synthetic material and a polymer.

31. The system of claim 28, wherein the interface surface is textured.

32. The system of claim 1, wherein at least one of the first gripping device and the second gripping device are one of freezing grips, hydraulic controllable grips, drum grips and custom grips capable of removably securing at least a portion of the specimen.

33. The system of claim 1, wherein, after the specimen is secured between the first gripping device and the second gripping device, the movable one of the first gripping device and the second gripping device is actuated, thereby exerting a load on the specimen.

34. The system of claim 33, wherein the exerted load is in one of a ramp profile, a step profile, a cyclic profile, a patterned profile, a predetermined profile, a user-specified load and a static load.

35. The system of claim 33, wherein the load data generated by the load exerted on the specimen is used to calculate at least one specimen property.

36. The system of claim 35, wherein the at least one specimen property is at least one of engineering stress, true stress, engineering strain, true strain, fatigue strength, creep characteristics, ultimate tensile strength, elastic modulus, contractile force, stiffness, toughness, ultimate stress, strain at ultimate stress, strain energy density and ultimate load.

37. The system of claim 1, wherein the image acquisition device includes a field of vision, and wherein a user is permitted to specify a portion of the specimen having at least one region of interest in the field of vision.

38. The system of claim 37, wherein the image data is used to calculate at least one cross-sectional area of the specimen in the specified region of interest.

39. The system of claim 38, wherein a specimen dimension is calculated by summing pixels across the specimen in the field of vision.

40. The system of claim 39, wherein the summed pixels are converted to a specified unit of measurement.

41. A computer-implemented method of determining mechanical properties of a deformable material specimen, comprising the steps of:
   (a) removably securing a first end of the specimen in a first gripping device;
   (b) removably securing a second end of the specimen in a second gripping device;
   (c) obtaining image data reflective of at least one physical dimension of at least a portion of the specimen at an initial state;
   (d) applying a load to the specimen by moving at least one of the first gripping device and the second gripping device;
   (e) measuring the displacement of the moved at least one of the first gripping device and the second gripping device, thereby producing displacement data;

(f) measuring the load placed upon the specimen, thereby producing load data; and (g) calculating at least one specimen property based at least partially upon the image data, the displacement data and the load data.

42. The method of claim 41, further comprising the step of obtaining image data reflective of at least one physical dimension of at least a portion of the specimen at a loaded state.

43. The method of claim 41, wherein the image data is obtained from an image acquisition device, the displacement data is obtained from a displacement measurement mechanism in communication with at least one of the first gripping device and the second gripping device and the load data is obtained from a load measurement mechanism in communication with at least one of the first gripping device and the second gripping device.

44. The method of claim 43, wherein the image acquisition device, the displacement measurement mechanism and the load measurement mechanism are in communication with a control mechanism, the method further comprising the step of receiving, by the control mechanism, at least one of respective image data, displacement data and load data therefrom.

45. The method of claim 44, wherein the displacement measurement mechanism is a linear variable differential transformer.

46. The method of claim 44, wherein the load measurement mechanism is a load cell.

47. The method of claim 44, wherein the image acquisition device includes a first camera device with a first camera device field of vision and a second camera device with a second camera device field of vision.

48. The method of claim 47, positioning the first camera device field of vision at 90 degrees with respect to the second camera device field of vision.

49. The method of claim 47, further comprising the step of specifying a portion of the specimen having at least one region of interest in at least one of the first camera device field of vision and the second camera device field of vision.

50. The method of claim 49, further comprising the steps of:

communicating the at least one region of interest between the first camera device and the second camera device; and duplicating the at least one region of interest on the first camera device and the second camera device.

51. The method of claim 49, wherein the physical dimension is at least one of width, diameter, depth and cross-sectional area of the specimen in the region of interest.

52. The method of claim 51, further comprising the steps of:

summing pixels across the specimen in the at least one of the first camera device field of vision and the second camera device field of vision; and calculating the cross-sectional area based upon the summation.

53. The method of claim 52, further comprising the step of converting the summed pixels to a specified unit of measurement.

54. The method of claim 47, further comprising the steps of:

directing the first camera device field of vision at a front surface of the specimen; and directing the second camera field of vision at a side surface of the specimen.

55. The method of claim 44, wherein the image acquisition device includes at least one field of vision, the method further comprising the step of directing the field of vision at a side surface of the specimen.

56. The method of claim 55, directing a light source towards a side surface of the specimen immediately opposite the side surface of the specimen upon which the field of vision is directed.

57. The method of claim 41, further comprising the step of displaying visual information and data directed to at least one of the image data, the displacement data and the load data to a user.

58. The method of claim 57, wherein the visual information and data is in a graphical format, a video format, an audiovisual format and a textual format.

59. The method of claim 41, wherein the image data is produced by an image acquisition device with a field of vision, the method further comprising the step of specifying a portion of the specimen having at least one region of interest in the field of vision.

60. The method of claim 41, wherein the physical dimension is at least one cross-sectional area of the specimen in the region of interest.

61. The method of claim 60, further comprising the steps of:

summing pixels across the specimen in the field of vision; and calculating the cross-sectional area based upon the summation.

62. The method of claim 61, further comprising the step of converting the summed pixels to a specified unit of measurement.

63. The method of claim 41, wherein the image data is produced by an image acquisition device with a field of vision, the method further comprising the step of directing the field of vision at a side surface of the specimen.

64. The method of claim 63, further comprising the step of directing a light source towards a side surface of the specimen immediately opposite the side surface of the specimen upon which the field of vision is directed.

65. The method of claim 41, wherein the image acquisition device is in communication with an image acquisition control mechanism configured to collect, process and transmit the image data.

66. The method of claim 41, wherein the specimen is one of soft tissue, biomaterial, deformable material, hard tissue, bio-artificial material and viscoelastic material.

67. The method of claim 41, wherein at least one of the first gripping device and the second gripping device are one of freezing grips, hydraulic controllable grips, drum grips and custom grips capable of removably securing at least a portion of the specimen.

68. The method of claim 41, wherein the exerted load is in one of a ramp profile, a step profile, a cyclic profile, a patterned profile, a predetermined profile, a user-specified load and a static load.

69. The method of claim 41, wherein the specimen property is at least one of engineering stress, true stress, engineering strain, true strain, fatigue strength, creep characteristics, ultimate tensile strength, elastic modulus contractile force, stiffness, toughness, ultimate stress, strain at ultimate stress, strain energy density and ultimate load.

70. The method of claim 41, further comprising the step of obtaining image data reflective of at least one physical dimension of at least a portion of the specimen at a loaded state.

71. The method of claim 41, wherein the image data is produced by an image acquisition device with a field of vision, the method further comprising the step of calibrating the field of vision prior to collecting image data relative to the specimen.

72. The method of claim 71, further comprising the step of obtaining image data reflective of at least one physical dimension of at least a portion of a calibration target.

73. The method of claim 72, wherein the calibration target is substantially similar in size and shape to at least a portion of the specimen.

74. The method of claim 73, further comprising the step of adjusting the field of vision of the image acquisition device by adjusting the position of the image acquisition device.

75. The method of claim 73, wherein the field of vision is adjusted in the x-direction, the y-direction, the z-direction, for pitch, for roll and for yaw.

76. The method of claim 73, wherein the image acquisition device includes a first camera device with a first camera device field of vision and a second camera device with a second camera device field of vision, the method further comprising the step of orienting at least one of the first camera device field of vision and the second camera device field of vision such that the field of vision is directed at a calibration target.

77. The method of claim 76, positioning the first camera device field of vision at 90 degrees with respect to the second camera device field of vision.

78. The method of claim 76, further comprising the step of orienting the first camera device field of vision and the second camera device field of vision such that both fields of vision are directed at a substantially similar area on the calibration target.

79. The method of claim 76, further comprising the step of calibrating the first camera device field of vision with the second camera device field of vision.

80. The method of claim 73, further comprising the steps of:
   detecting opposite edge locations on a calibration target; and
   summing pixels between the opposite edge locations in the field of vision.

81. The method of claim 80, further comprising the steps of:
   repeating the steps of claim 80 for a plurality of opposite edge locations on the calibration target; and
   calculating an average summation for the plurality of opposite edge locations.

82. The method of claim 80, further comprising the step of converting the summed pixels to a specified unit of measurement.

83. The method of claim 71, further comprising the step of specifying a portion of a calibration target having at least one region of interest in the field of vision.

84. The method of claim 41, wherein the image data is produced by an image acquisition device with a field of vision, the method further comprising the step of specifying a portion of the specimen having a plurality of substantially evenly spaced region of interest lines in the field of vision.

85. The method of claim 84, further comprising the steps of:
   detecting opposite edge locations on the specimen; and
   summing pixels between the opposite edge locations in the field of vision.

86. The method of claim 85, further comprising the step of repeating the steps of claim 80 for a plurality of opposite edge locations on the specimen.

87. The method of claim 85, further comprising the step of repeating the steps of claim 80 at a plurality of time points.

88. The method of claim 87, wherein the repeating step is performed when the specimen is in a loaded state.

89. The method of claim 85, further comprising the step of converting the summed pixels to a specified unit of measurement.

90. The method of claim 84, further comprising the steps of:
   detecting opposite edge locations on the specimen on at least two separate specimen surfaces; and
   summing pixels between the opposite edge locations in the field of vision.

91. The method of claim 90, further comprising the step of repeating the steps of claim 84 for a plurality of opposite edge locations on the specimen.

92. The method of claim 90, further comprising the step of repeating the steps of claim 84 at a plurality of time points.

93. The method of claim 92, wherein the repeating step is performed when the specimen is in a loaded state.

94. The method of claim 41, further comprising the step of substantially centering the specimen with respect to the first gripping device and the second gripping device.

95. The method of claim 41, wherein the specimen is substantially taut between the first gripping device and the second gripping device.

96. The method of claim 41, further comprising the step of vertically aligning the specimen.

97. The method of claim 41, further comprising the steps of displaying the image data simultaneously with at least one of the displacement data, the load data and the calculated specimen property.

98. The method of claim 97, wherein the data is displayed in a real-time format.

99. The method of claim 41, further comprising the step of specifying a data collection rate for the image data in frames per second.

100. The method of claim 41, further comprising the step of specifying a desired specimen property to be calculated.

101. The method of claim 41, wherein the image data is produced by an image acquisition device with a field of vision, the method further comprising the steps of:
   moving the image acquisition device with respect to the specimen; and
   optimizing the field of vision with respect to a geometric measurement of a specified portion of the specimen.

102. A system for measuring mechanical properties of a deformable material specimen, comprising:
   a first gripping device configured to removably secure a first end of the specimen;
   a second gripping device configured to removably secure a second end of the specimen; and
   at least one image acquisition device configured to produce image data reflective of a specified area of the specimen;
   wherein at least one of the first gripping device and the second gripping device is movable in a first direction and in communication with a linear variable differential transformer configured to produce displacement data reflective of position of the at least one of the first gripping device and the second gripping device;
   wherein at least one of the first gripping device and the second gripping device is in communication with a load cell configured to produce load data reflective of the force experienced by the at least one of the first gripping device and the second gripping device;

the system further comprising a control mechanism in communication with the image acquisition device, the linear variable differential transformer and the load cell, the control mechanism configured to:

(i) at least one of receive, process and transmit the image data, the displacement data and the load data; and (ii) calculate at least one specimen property based at least partially upon the image data, the displacement data and the load data.

\* \* \* \* \*